(12) United States Patent
Wiebe et al.

(10) Patent No.: US 7,683,187 B2
(45) Date of Patent: Mar. 23, 2010

(54) PROCESS FOR PRODUCING DELTA-LACTONES

(75) Inventors: Lars Wiebe, Grindsted (DK); Thomas Schmidt, Haderslev (DK)

(73) Assignee: Danisco A/S, Copenhagen (DK)

( * ) Notice: Subject to any disclaimer, the term of this patent is extended or adjusted under 35 U.S.C. 154(b) by 141 days.

(21) Appl. No.: 11/738,338

(22) Filed: Apr. 20, 2007

(65) Prior Publication Data

US 2007/0249849 A1    Oct. 25, 2007

Related U.S. Application Data

(63) Continuation-in-part of application No. PCT/IB2005/003436, filed on Oct. 25, 2005.

(30) Foreign Application Priority Data

| Oct. 27, 2004 | (GB) | ................................. | 0423874.7 |
| Sep. 8, 2005 | (GB) | ................................. | 0518353.8 |

(51) Int. Cl.
C07D 307/02 (2006.01)
C07D 305/12 (2006.01)

(52) U.S. Cl. ...................................... 549/295; 549/308

(58) Field of Classification Search ................. 549/295, 549/308
See application file for complete search history.

(56) References Cited

U.S. PATENT DOCUMENTS

| 3,061,614 | A | * | 10/1962 | Sweeney et al. | ............. | 549/295 |
| 3,952,020 | A |   | 4/1976  | Stapp |  |  |
| 4,069,232 | A |   | 1/1978  | Horvitz et al. |  |  |
| 4,309,352 | A |   | 1/1982  | Ho |  |  |
| 5,731,225 | A | * | 3/1998  | Yamamori | ................... | 438/653 |
| 5,767,321 | A | * | 6/1998  | Billig et al. | ................. | 568/454 |
| 5,883,265 | A | * | 3/1999  | Tjaden et al. | ................ | 549/266 |
| 5,952,530 | A | * | 9/1999  | Argyropoulos et al. | ..... | 568/454 |
| 6,294,700 | B1| * | 9/2001  | Kanel et al. | .................. | 568/454 |
| 6,307,065 | B1| * | 10/2001 | Tjaden et al. | ................ | 549/266 |
| 2001/0053858 | A1 |  | 12/2001 | Tjaden et al. |  |  |

FOREIGN PATENT DOCUMENTS

| DE | 2 134 094 | 1/1972 |
| DE | 195 30 549 | 2/1997 |
| EP | 0 176 370 | 4/1986 |
| EP | 0 341 773 | 11/1989 |
| EP | 0 844 994 B1 | 5/1999 |
| GB | 1 355 668 | 7/1971 |
| GB | 1355667 | 6/1974 |
| WO | WO 00/35899 | 6/2000 |

OTHER PUBLICATIONS

Imai et al. Synthesis 395, 1993.*
Breit European Journal of Organic Chemistry, 1998, 1123-1134.*
Tanaka et al. Journal of organic chemistry 1991, 56, 4333-4334.*
Alper et al. Journal of Chemical Soceity, Chemical Communication, 511, 1985.*
Houllemare et al. Journal of Chemical Soceity, Perkin I, 1629, 1997.*
Sarangi et al. (Tetrahedron Letters, 7119-7122, 1995.*
Howard Alper, et al., Palladium-Catalysed Conversion Of Alkenols Into Five- And Six-Membered Ring Lactones At Room Temperature And Atmospheric Pressure, J. Chem. Soc. Chem. Commun. (1985) vol. 8, p. 511-512.
Bernhard Breit, 1,3-Asymmetric Induction In Stereoselective Rhodium-Catalyzed Hydroformylation Of Homomethallylic Alcohols, Eur. J. Org. Chem. (1998) vol. 6, p. 1123-1134.
Yuan L. Chow, et al., A New Synthesis Of Lactones From Tertiary Alkenylcarbinols By Cobalt-Catalyzed Photocarbonylation Under Ambient Conditions, Can. J. Chem. (1995) vol. 73, p. 740-742.
Didier Houllemare, et al., Synthesis Of Homoallylic (but 3-enylic) Alcohols From Aldehydes With Allylic Chlorides, Tin (II) Chloride And Potassium Iodide In Water, J. Chem. Soc. Perkin Trans. (1997) vol. 1, 1629-1632.
Toshiro Imai, et al., A Mild And Convenient Barbier-Type Allylation Of Aldehydes To Homoallylic Alcohols Via Iodide Ion Promoted Stannylation Of Allylic Bromides And Chlorides With Tin (II) Chloride, Synthesis (1993) vol. 4, 395-399.
Chintamani Sarangi, et al., A Novel Cu(II)-Mg-System For Allylation And Reduction Of Carbonyl Compounds, Tetrahedron Letters (1995) vol. 36, No. 39, p. 7119-7122.
Koichi Tanaka, et al., Reformatsky And Luche Reaction In The Absence Of Solvent, J. Org. Chem. (1991) vol. 56, p. 4333-4334.
Zhang, "Fine Chemicals", 2001, vol. 18, No. 4, pp. 206-206 and 231 (Chinese with English abstract).

* cited by examiner

*Primary Examiner*—D. Margaret Seaman
*Assistant Examiner*—Nizal S Chandrakumar
(74) *Attorney, Agent, or Firm*—Frommer Lawrence & Haug LLP; Thomas J. Kowalski; Heather J. Dipietrantonic

(57) ABSTRACT

The present invention relates to a process for preparing a lactone. The process comprises the steps of reacting an aldehyde with an organic halide in a carbon chain extension reaction to form an alcohol compound comprising a functional group capable of allowing for carbonylation of said alcohol compound, and then reacting said alcohol compound in a carbonylation reaction to form an hydroxycarboxylic acid; and cyclizing the hydroxycarboxylic acid to produce the lactone.

17 Claims, 13 Drawing Sheets

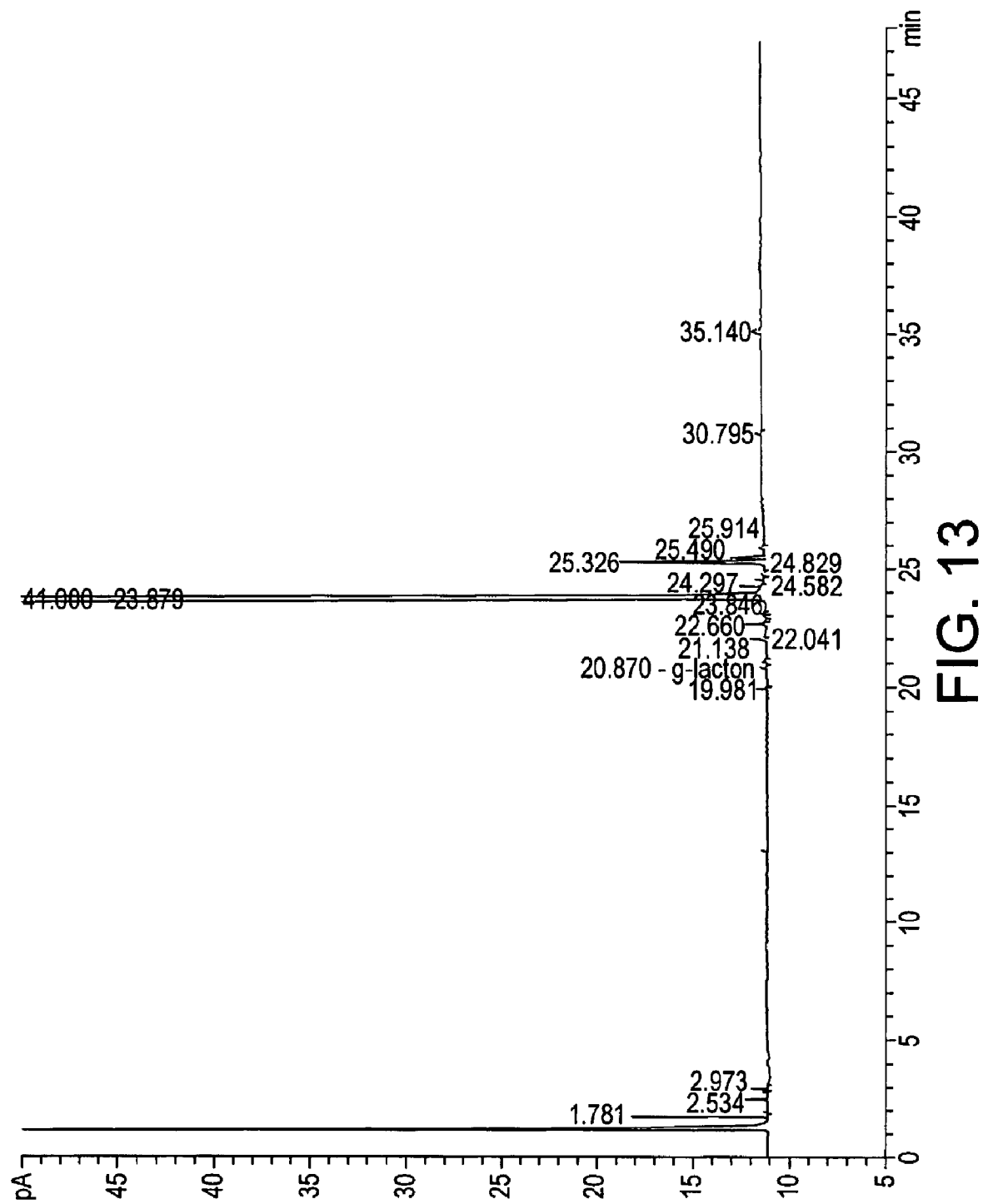

PROCESS FOR PRODUCING DELTA-LACTONES

REFERENCE TO RELATED APPLICATIONS

This application is a continuation-in-part of International Patent Application PCT/IB2005/003436 filed Oct. 25, 2005 and published as WO 2006/046140 on May 4, 2006, which claims priority from Great Britain Patent Application Nos. 0518353.8 filed Sep. 8, 2005 and 0423874.7 filed Oct. 27, 2004.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF THE INVENTION

The present invention relates to a process.

In particular, the present invention relates to a process for preparing lactones, such as gamma- and delta-lactones.

BACKGROUND TO THE INVENTION

Lactones, in particular gamma- and delta-lactones, are known to possess useful organoleptic properties and are important flavour and aroma constituents in many natural products. Gamma- and delta-lactones possess a chiral center and can occur in both enantiomeric forms. However, in nature the "R" chiral forms tend to be predominant (especially as the alkyl chain length increases). Naturally occurring gamma-lactones are found mainly in plants, whilst delta-lactones are found mainly in animals.

As a result of these properties, lactones have been employed as flavour and fragrance materials. These materials have a high flavour value due to their extremely low odour thresholds which average about 0.1 parts per million. For example, delta-decalactone, or 5-pentylpentanolide, ($C_{10}H_{18}O_2$) has an odour detection threshold (in water) of 100 parts per billion, and occurs in products as diverse as Apricot, Blue Cheese, Burley Tobacco, Butter, Coconut, Mango, Peach, Raspberry, Rum, Strawberry and Tea.

In theory naturally occurring lactones may be isolated from plant material, for example, by extraction or distillation. However, in practice this is often impractical or impossible because the lactones are present in extremely low concentrations. Consequently, synthetic methods are often used to manufacture lactones for use as flavour and fragrance materials.

In using flavouring compounds, it has often been seen as important to be able to designate the flavouring compound as "natural". As a result, research into synthetic methods of preparing flavouring compounds have tended to concentrate on obtaining the desired compound by physical, enzymatic or microbiological processes from a product of plant or animal origin, rather than from products derived from petrochemicals for example.

Thus, Cardillo et al., 1989, J. Org. Chem. 54, 4979-4980, have described the conversion of $C_{14}$-$C_{19}$ gamma-hydroxy alkene fatty acids into $C_8$ and $C_{11}$ delta-lactones and $C_9$, $C_{10}$ and $C_{11}$ gamma-lactones in *Cladiosporium suaveolens*. The substrates are known to be present in nature, but there is no readily available source U.S. Pat. No. 4,560,656 discloses the preparation of gamma-hydroxy-decanoic acid and subsequently of gamma-decalactone from castor oil or castor oil hydrolysate with specific microorganisms.

EP-A-0258993 discloses how to use ricinoleic acid as the substrate and other microorganisms are specified. However, the microorganisms mentioned are not generally recognised as "food grade". Moreover, there is a need for processes that can produce higher quantities of lactones than those disclosed.

U.S. Pat. No. 5,215,901 discloses a process for producing delta-lactones on an industrial scale by using a micro-organism cultured in a culture medium containing a suitable substrate for producing delta-hydroxy-alkanoic acids. The micro-organism either does not metabolize delta-lactones, or only metabolises them very slowly. The micro-organism is cultured aerobically in a culture medium containing a hydroxy fatty acid having an odd number of carbon atoms between the carboxyl group and the carbon atom carrying the hydroxyl group. The micro-organism is cultured under such conditions and for a period of time sufficient to produce at least 0.1 g of delta-hydroxy-alkanoic acid per kg of fermentation broth. Then the delta-hydroxy-alkanoic acid is converted to the corresponding delta-lactone at a pH below 7. The delta-lactone is recovered substantially free from the original hydroxy fatty acid. The applicable micro-organisms are capable of effecting beta-oxidation of the hydroxy fatty acids used as starting materials. Examples of such micro-organisms may be bacteria, yeasts or filamentous fungi.

Purely chemical synthetic routes to produce lactones are also known. For example, a hydroxycarboxylic acid, Ia, which contains both an alcohol and a carboxylic acid functional group, can undergo an acid catalysed intramolecular esterification to produce a lactone, IIa. This lactonization process is an equilibrium reaction that is favoured if the lactone formed has a five- or six-membered ring. Lactones containing larger ring sizes may be produced by for example, removing the water produced in the reaction so as to move the unfavourable equilibrium towards the lactone.

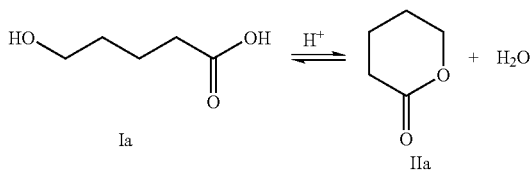

Many gamma- and delta-lactones are formed so readily from the hydroxycarboxylic acids that it is not even necessary to add acid to catalyse the intramolecular esterification reaction.

EP-A-0176370 discloses the production of lactones, such as IIb, by reacting an unsaturated alcohol, such as IIIa, with carbon monoxide in the presence of a protonic acid and a catalyst comprising (a) at least one of the metals palladium, rhodium, ruthenium, iridium and cobalt, and (b) at least one of the metals copper, molybdenum and iron with (a) and (b) being in the form of either the elemental metal or a compound thereof. This process produced gamma- and delta-lactones in moderate to good yields, 15-80%.

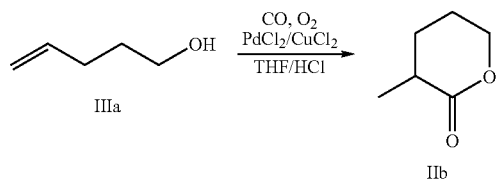

Thus, there is a continuing need for improved processes for producing lactones.

DETAILED ASPECT OF THE PRESENT INVENTION

According to one aspect of the present invention there is provided a process for preparing a lactone comprising the steps of:

reacting a carbonyl compound selected from a group consisting of an aldehyde and a ketone with an organic halide in a carbon chain extension reaction to form an alcohol compound comprising a functional group capable of allowing for carbonylation of said alcohol compound;

reacting said alcohol compound in a carbonylation reaction to form an hydroxycarboxylic acid; and cyclising the hydroxycarboxylic acid to produce the lactone.

As used herein, the term "carbonylation reaction" is any reaction which introduces a carbonyl group into an organic compound. For example, the carbonylation reaction may be a hydrocarboxylation reaction.

In a further aspect of the invention, there is provided a use of a lactone obtained according to the process of the present invention, as a food flavouring.

In another aspect of the invention, there is provided a method of flavouring a food material comprising contacting a lactone obtained according to the process of the present invention to at least one other food ingredient.

The present invention also provides a method of preparing a food or a food ingredient, the method comprises admixing a lactone obtained according to any one of the process of the present invention with at least one other food ingredient. The method for preparing a food or a food ingredient is another aspect of the present invention.

Preferable Aspects

Carbonyl Compound

A carbonyl compound is a compound comprising a carbonyl group, C=O.

In a preferred aspect, the carbonyl compound is of Formula IVa

wherein $R_{1A}$ is a hydrocarbyl group, and $R_{1B}$ is selected from hydrogen and a hydrocarbyl group.

More preferably $R_{1A}$ is a $C_1$-$C_8$ alkyl group optionally substituted with one or more hydrocarbyl or oxyhydrocarbyl groups.

More preferably $R_{1A}$ is a $C_5$-$C_7$ alkyl group.

Preferably, $R_{1B}$ is hydrogen or a $C_1$-$C_8$ alkyl group optionally substituted with one or more hydrocarbyl or oxyhydrocarbyl groups. Preferably $R_{1B}$ is a $C_5$-$C_7$ alkyl group.

More preferably $R_{1B}$ is hydrogen, so that the carbonyl compound is an aldehyde.

$R_{1A}$ and $R_{1B}$ may be the same or different. Preferably $R_{1A}$ and $R_{1B}$ are different.

In a further aspect of the present invention the carbonyl compound is of formula IVa, and $R_{1B}$ is a hydrocarbyl group which is further attached at any point to $R_{1A}$ to form a cyclic ketone. For example, $R_{1A}$ is a —$CH_2$— group and $R_{1B}$ is a —$(CH_2)_4$— group which is attached to $R_{1A}$ to form cyclohexanone. Where a cyclic ketone such as, for example, cyclohexanone or cyclopentanone is used, the lactone produced by the present invention is a spiro compound.

Hydrocarbyl

In the context of the present invention, the term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, Or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In some aspects of the present invention, one or more hydrocarbyl groups is independently selected from $C_1$-$C_{20}$ alkyl group, $C_1$-$C_{15}$ alkyl group, $C_1$-$C_{12}$ alkyl group, $C_1$-$C_{10}$ alkyl group, such as $C_1$-$C_6$ alkyl group, and $C_1$-$C_3$ alkyl group. Typical alkyl groups include $C_1$ alkyl, $C_2$ alkyl, $C_3$ alkyl, $C_4$ alkyl, $C_5$ alkyl, $C_6$ alkyl, $C_7$ alkyl, and $C_8$ alkyl.

In some aspects of the present invention, one or more hydrocarbyl groups may be independently selected from one or more oxyhydrocarbyl groups.

Oxyhydrocarbyl

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Organic Halide

In a preferred aspect of the present invention, the organic halide is an unsaturated organic halide.

Preferably, the organic halide is an unsaturated halide of the Formula IIIb:

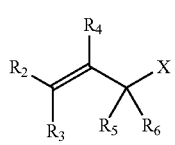

IIIb wherein $R_2$, $R_3$, $R_4$, $R_5$ and $R_6$ are independently selected from a group comprising a hydrogen and a hydrocarbyl group; and X is a halide.

Preferably $R_2$, $R_3$, $R_4$, $R_5$ and $R_6$ are independently selected from a group comprising hydrogen and a $C_1$-$C_4$ alkyl group, preferably a methyl group.

Preferably $R_2$ and/or $R_3$ is an alkyl group.

Preferably the halide is selected from chlorine, bromine and iodine.

Preferably the organic halide is an allyl halide.

More preferably the organic halide is allyl chloride.

In a further aspect of the present invention, the organic halide is an unsaturated organic halide of the Formula IIIc

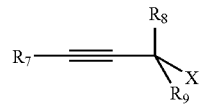

IIIc wherein $R_7$, $R_8$ and $R_9$ are independently selected from a group comprising a hydrogen and a hydrocarbyl group; and X is a halide.

Preferably $R_7$, $R_8$ and $R_9$ are independently selected from a group comprising hydrogen and a $C_1$-$C_4$ alkyl group, preferably a methyl group.

Carbon Chain Extension Reaction

The term carbon chain extension reaction is used in its normal sense of adding one or more carbon containing components to an organic molecule to form a new carbon-carbon bond.

Preferably the carbon chain extension reaction is a Barbier-type reaction, and this reaction may use any catalyst suitable for the Barbier reaction. Alternatively, the carbon chain extension reaction may be a Grignard-type reaction.

Preferably the carbon chain extension reaction uses a catalyst comprising a metal and/or a salt of a metal wherein the metal is selected from aluminium, antimony, bismuth, cadmium, copper, indium, lead, tin, magnesium, manganese, sodium, zinc and mixtures thereof.

More preferably the catalyst in the carbon chain extension reaction is a mixture of copper and tin(II) chloride.

More preferably the catalyst in the carbon chain extension reaction comprising a metal and/or a salt of a metal wherein the metal comprises a mixture of aluminium, copper, tin and sodium. More preferably, the catalyst comprises a mixture of aluminium, copper, tin (II) chloride and sodium iodide.

The carbon chain extension reaction may be carried out in an aqueous mixture of an organic solvent, for example, in an aqueous mixture of tetrahydrofuran (THF).

Preferably the carbon chain extension reaction is carried out in water. Water is the preferred solvent as its use simplifies the purification procedure at the end of the reaction and is more environmentally friendly than most organic solvents. Ideally, the reaction mixture is stirred to mix the 2-phase system effectively and, therefore, to reduce the reaction time. Once the reaction is complete the aqueous phase, which contains the catalyst, can be simply separated from the organic phase which contains the crude product.

Preferably the carbon chain extension reaction is carried out at ambient temperature as high temperatures may lead to unwanted side reactions such as aldol addition/condensation. Preferable the carbon chain extension reaction is carried out at a temperature of from 5 to 100° C., preferably from 10 to 100° C., from 10 to 80° C., from 10 to 50° C.; from 10 to 40° C.; from 15 to 100° C.; from 15 to 80° C.; from 15 to 50° C.; from 15 to 40° C.

Preferably the ratio of aldehyde to organic halide is from about 1:1 to 1:5. More preferably the ratio of aldehyde to organic halide is from about 1:1 to 1:3.

Alcohol Compound

Preferably the functional group capable of allowing for carbonylation of the alcohol compound is an alkene functional group.

Preferably the alcohol compound is a homoallylic alcohol.

Carbonylation Reaction

Preferably, the carbonylation reaction is a hydrocarboxylation reaction.

Preferably the carbonylation reaction comprises reacting the alcohol compound with a source of carbon monoxide.

Preferably the source of carbon monoxide is carbon monoxide, formic acid or oxalic acid.

Preferably the carbonylation reaction uses a catalytic system comprising a transition metal and/or a salt of a transition metal.

Preferably the carbonylation reaction uses a catalytic system comprising a transition metal and/or a salt of a transition metal wherein the transition metal is selected from cobalt, iridium, nickel, palladium, platinum, rhodium, ruthenium, and mixtures thereof.

More preferably the carbonylation reaction catalytic system comprises palladium chloride.

Preferably, the carbonylation reaction catalytic system further comprises a ligand. Ligands form coordination compounds or complexes with an acceptor (Lewis acid) by means of a lone pair of electrons. Where the ligand is composed of a number of atoms, the one which is directly attached to the acceptor is called the donor atom.

Preferably the ligand comprises at least one donor atom selected from nitrogen, phosphorous, arsenic, antimony and bismuth.

More preferably the ligand comprises at least one donor atom selected from nitrogen and phosphorous.

If the transition metal used in the catalytic system in the carbonylation reaction is cobalt, the ligand preferably comprises at least one nitrogen donor atom. Preferably, the ligand is pyridine optionally substituted with one or more hydroxy; alkyl, especially lower ($C_1$-$C_6$) alkyl (e.g. methyl, ethyl, n-propyl, isopropyl, n-butyl, sec-butyl, tert-butyl, n-pentyl and other pentyl isomers, and n-hexyl and other hexyl isomers); alkoxy, especially lower ($C_1$-$C_6$) alkoxy (e.g. methoxy, ethoxy, propoxy etc.); alkinyl (e.g. ethinyl); or halogen (e.g. fluoro, chloro, bromo, iodo) substituents.

More preferably the ligand is triphenylphosphine. Triphenylphosphine is relatively cheap compared to many other available ligands. In addition, good yields and selectivities are observed in the carbonylation reaction when triphenylphosphine is used as the ligand.

Preferably the catalytic system further comprises a metal co-catalyst.

More preferably the metal co-catalyst is a tin compound; preferably a tin(II) halide, preferably tin(II) chloride.

Preferably the carbonylation reaction is carried out at a temperature of from 80 to 140° C.

Preferably the carbonylation reaction is carried out at an absolute pressure of from 1 to 150 bara, more preferably at a pressure of from 5 to 150 bara, preferably 5 to 100 bara, preferably 5 to 50 bara.

The preferred pressure for the carbonylation reaction may vary depending on the particular catalytic system used in the reaction. For example, if the catalytic system comprises cobalt then the pressure used will be toward the higher end of the above ranges, for example, a pressure around 100 bara.

Preferably the carbonylation reaction is carried out using a solvent system comprising toluene.

Preferably when the source of carbon monoxide is carbon monoxide, the carbonylation reaction is carried out in the presence of water. Under such conditions the product of the carbonylation reaction may spontaneously cyclise to give the desired lactone. For example, 4-hydroxy-1-alkenes can react with carbon monoxide under the preferred reaction conditions (i.e. catalyst, temperature, pressure and in the presence of water) to give 5-hydroxycarboxylic acids. These 5-hydroxycarboxylic acids may cyclise under the carbonylation reaction conditions to produce the corresponding delta-lactone.

Alternatively, the carbonylation reaction may be carried out in the presence of hydrogen, a source of carbon monoxide and the absence of water. This carbonylation reaction is commonly called a hydroformylation reaction. This alternative produces an aldehyde as an intermediate which requires a further oxidation step in order to give the desired hydroxycarboxylic acid. Suitable oxidising agents would be readily apparent to a skilled person. For example, the further oxidation may be carried out using a silver oxide catalyst, or with $NaClO_2/H_2O_2$. Generally, the hydroxycarboxylic acid will cyclise spontaneously, however, with proper choice of the reaction conditions, the hydroxycarboxylic acid may be isolated.

Process

Preferably the process further comprises the step of purifying the lactone.

Preferably the step of purifying the lactone comprises distillation of the lactone.

In a further aspect, the invention provides a process for preparing a delta-lactone comprising the steps of:

a) reacting an aldehyde with an unsaturated organic halide in a carbon chain extension reaction, using a catalyst comprising a metal and/or a salt of a metal wherein the metal is selected from aluminium, antimony, bismuth, cadmium, copper, indium, lead, tin, magnesium, manganese, sodium, zinc and mixtures thereof, to form an alcohol compound comprising a functional group capable of allowing for carbonylation of said alcohol compound;

b) reacting said alcohol compound with a source of carbon monoxide in a carbonylation reaction in the presence of water, using a catalytic system comprising a transition metal and/or a salt of a transition metal wherein the transition metal is selected from cobalt, iridium, palladium, platinum, rhodium, and mixtures thereof, and a ligand comprising at least one donor atom selected from nitrogen, phosphorous, arsenic, antimony and bismuth to form an hydroxycarboxylic acid; and c) cyclising the hydroxycarboxylic acid to produce the delta-lactone.

Preferably, the process further comprises a step d) purifying the delta-lactone.

Preferably the step d) comprises distillation of the lactone.

Compound

The term "compound" is intended to encompass isomeric forms (such as stereoisomers and/or geometric and/or optical isomers, and mixtures thereof), chemical derivatives, mimetics, solvates and salts of the compounds.

Stereo and Geometric Isomers

Some of the compounds/agents of the present invention may exist as stereoisomers and/or geometric isomers—e.g. they may possess one or more asymmetric and/or geometric centres and so may exist in two or more stereoisomeric and/or geometric forms. Where a compound and/or agent contains an alkenyl or alkenylene group, cis (E) and trans (Z) isomerism may also occur. The present invention contemplates the use of all of the individual stereoisomers and geometric isomers of those compounds, and mixtures thereof. The terms used in the claims encompass these forms, provided said forms retain the appropriate functional activity (though not necessarily to the same degree).

Separation of diastereoisomers or cis and trans isomers may be achieved by conventional techniques, e.g. by fractional crystallisation, chromatography, distillation or H.P.L.C. or any combination(s) thereof, of a stereoisomeric mixture of the agent or a suitable salt or derivative thereof. An individual enantiomer of the compound and/or agent may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Forms

The lactones produced according to the process of the present invention are generally liquids and are typically used in solution. However, they can be supplied on a solid, or even in the form of a release formulation. Preferably such release formulations provide controlled release. For example, the formulation may result in the encapsulation of the lactone compound to provide slow release, or the formulation may provide release under certain conditions such as within a particular pH range. Alternatively, the lactones may be formulated as salts such as alkali metal salts or alkaline earth metal salts. Preferably the salt will be the sodium, magnesium or calcium salt.

Isolated

In one aspect, preferably the lactone is in an isolated form. The term "isolated" means that the lactone is at least substantially free from at least one other component with which the lactone is naturally associated in nature and as found in nature.

Purified

In one aspect, preferably the lactone is in a purified form. The term "purified" means that the lactone is in a relatively pure state—e.g. at least about 90% pure, or at least about 95% pure or at least about 98% pure.

Combination with Other Components

The lactones prepared by the process of the present invention may be used in combination with other components. Such compositions can lead to improved aroma, flavour, mildness, consistency, texture, body, mouth feel, firmness, viscosity, gel fracture, structure and/or organoleptic properties and nutrition of products for consumption containing said composition. Furthermore, these composition can also be used in combination with other components of products for consumption to deliver said improvements Examples of other components include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

As used herein the term "thickener or gelling agent" as used herein refers to a product that prevents separation by slowing or preventing the movement of particles, either droplets of immiscible liquids, air or insoluble solids.

The term "stabiliser" as used here is defined as an ingredient or combination of ingredients that keeps a product (e.g. a food product) from changing over time.

The term "emulsifier" as used herein refers to an ingredient (e.g. a food product ingredient) that prevents the separation of emulsions.

As used herein the term "binder" refers to an ingredient (e.g. a food ingredient) that binds the product together through a physical or chemical reaction.

The term "crystal modifier" as used herein refers to an ingredient (e.g. a food ingredient) that affects the crystallisation of either fat or water.

"Carriers" or "vehicles" mean materials suitable for compound administration and include any such material known in the art such as, for example, any liquid, gel, solvent, liquid diluent, solubiliser, or the like, which is non-toxic and which does not interact with any components of the composition in a deleterious manner.

Examples of nutritionally acceptable carriers include, for example, water, salt solutions, alcohol, silicone, waxes, petroleum jelly, vegetable oils, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

As used herein the term "component suitable for animal or human consumption" means a compound which is or can be added to the composition of the present invention as a supplement which may be of nutritional benefit, a fibre substitute or have a generally beneficial effect to the consumer.

By way of example, the components may be prebiotics such as polydextrose (PDX), alginate, xanthan, pectin, locust bean gum (LBG), inulin, guar gum, galacto-oligosaccharide (GOS), fructo-oligosaccharide (FOS), lactosucrose, soybean oligosaccharides, palatinose, isomalto-oligosaccharides, gluco-oligosaccharides and xylo-oligosaccharides.

Food

The lactones produced by the process of the present invention may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

Food Ingredient

The lactones produced by the process of the present invention may be used as—or may be added to—a food ingredient.

As used herein the term "food ingredient" includes a formulation, which is or can be added to functional foods or foodstuffs and includes formulations which can be used at low levels in a wide variety of products that require, for example, acidifying or emulsifying.

The food ingredient may be in the form of a solution or as a solid—depending on the use and/or the mode of application and/or the mode of administration.

Food Supplements

The lactones produced by the process of the present invention may be—or may be added to—food supplements.

Functional Foods

The lactones produced by the process of the present invention may be—or may be added to—functional foods.

As used herein, the term "functional food" means food which is capable of providing not only a nutritional effect and/or a taste satisfaction, but is also capable of delivering a further beneficial effect to consumer.

Although there is no legal definition of a functional food, most of the parties with an interest in this area agree that they are foods marketed as having specific health effects.

Food Products

The lactones produced by the process of the present invention can be used in the preparation of food products such as one or more of: confectionery products, dairy products, meat products e.g. sausages, poultry products, fish products and bakery products and other consumables e.g. jams and jelly.

By way of example, the lactones produced by the process of the present invention can be used as ingredients to soft drinks, a fruit juice or a beverage comprising whey protein, health teas, cocoa drinks, milk drinks and lactic acid bacteria drinks, yoghurt, drinking yoghurt and wine.

Fragrances

The lactones produced by the process of the present invention can be used in the preparation of fragrances and perfumes.

EXAMPLES

Material and Methods

Gas chromatography-mass spectrometry (GC-MS) was performed using a GC/MS 6890/5973 from Agilent Technologies. The samples were prepared by diluting 1-2 drops of the sample in diethyl ether. The gas chromatography (GC) was carried out using the following settings:

| | |
|---|---|
| Injection: | 1 μl with split ratio 1:25 |
| Injector temperature: | 260° C. |
| Column: | 25 m × 0.25 mmID × 0.25 μm FFAP capillary column from Quadrex |
| Carrier gas: | He at 0.8 ml/minute |
| Oven program: | 37° C. fro 4 minutes, then 5° C./minute to 240° C., hold 20 minutes |

The mass spectrometry (MS) was carried out using the following settings:

Scan range 26-300 amu (1-18 minutes)

Scan range 26-450 amu (from 18 minutes)

$^1$H NMR spectra were recorded at 200 MHz on a Varian Mercury 200/54 spectrometer, using a 20 μL sample in 700 μL CDCl$_3$ (locking and solvent) Tetramethyl silane (TMS) was used as 0.0 ppm reference line.

$^{13}$C NMR spectra were recorded at 50.3 MHz on a Varian Gemini200 spectrometer, using a 100 μL sample in 700 μL CDCL$_3$.

Example 1

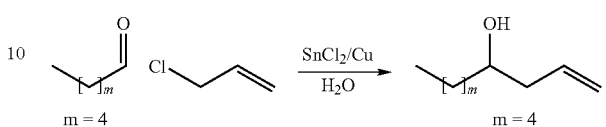

3500 ml water, 200 g hexanal (2 mol) and 305 g allyl chloride (4 mol), 900 g tin(II) chloride dihydrate (2 mol) and 25 g copper powder (0.4 mol) was added into a 6 l flask. The reaction mixture was stirred at ca. 30° C. for 8 h. The organic phase was separated by decantation or centrifugation and the crude raw product distilled in vacuo to give 4-hydroxy-1-nonene. MS: m/z 141 (M-1), 101 (M-C3H5), 124 (M-18), 83 (101-18), 55 (83-C2H4).

Example 2

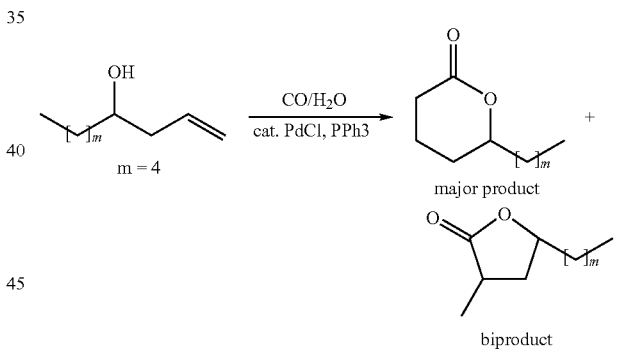

Figure 1:
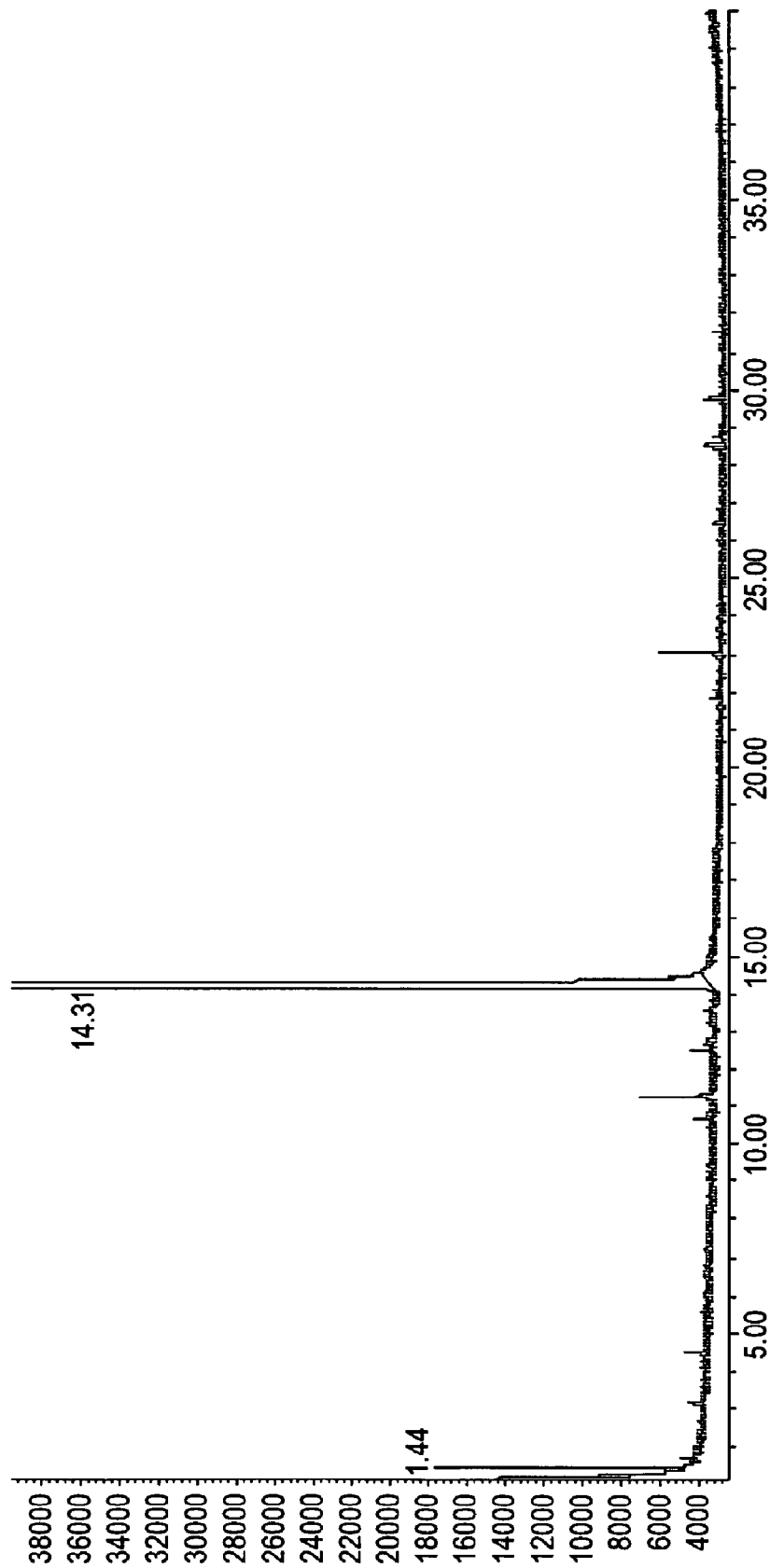
FIG. 1 shows a gas chromatographic analysis after distillation of the crude raw product. This indicates that the desired alcohol compound was >98% pure.
Figure 2:
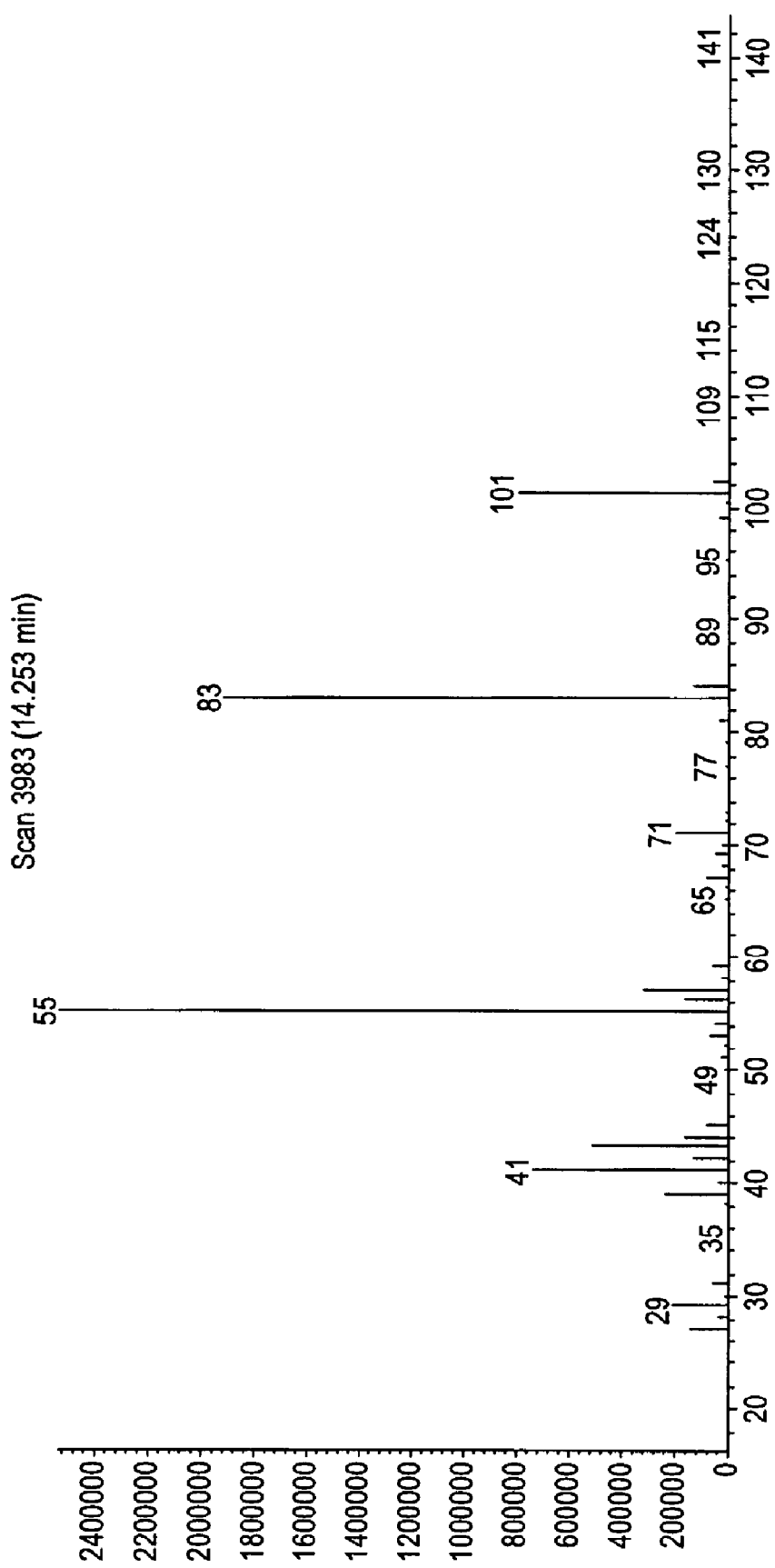
FIG. 2 shows the mass spectra for the major peak in the GC trace.
Figure 3:
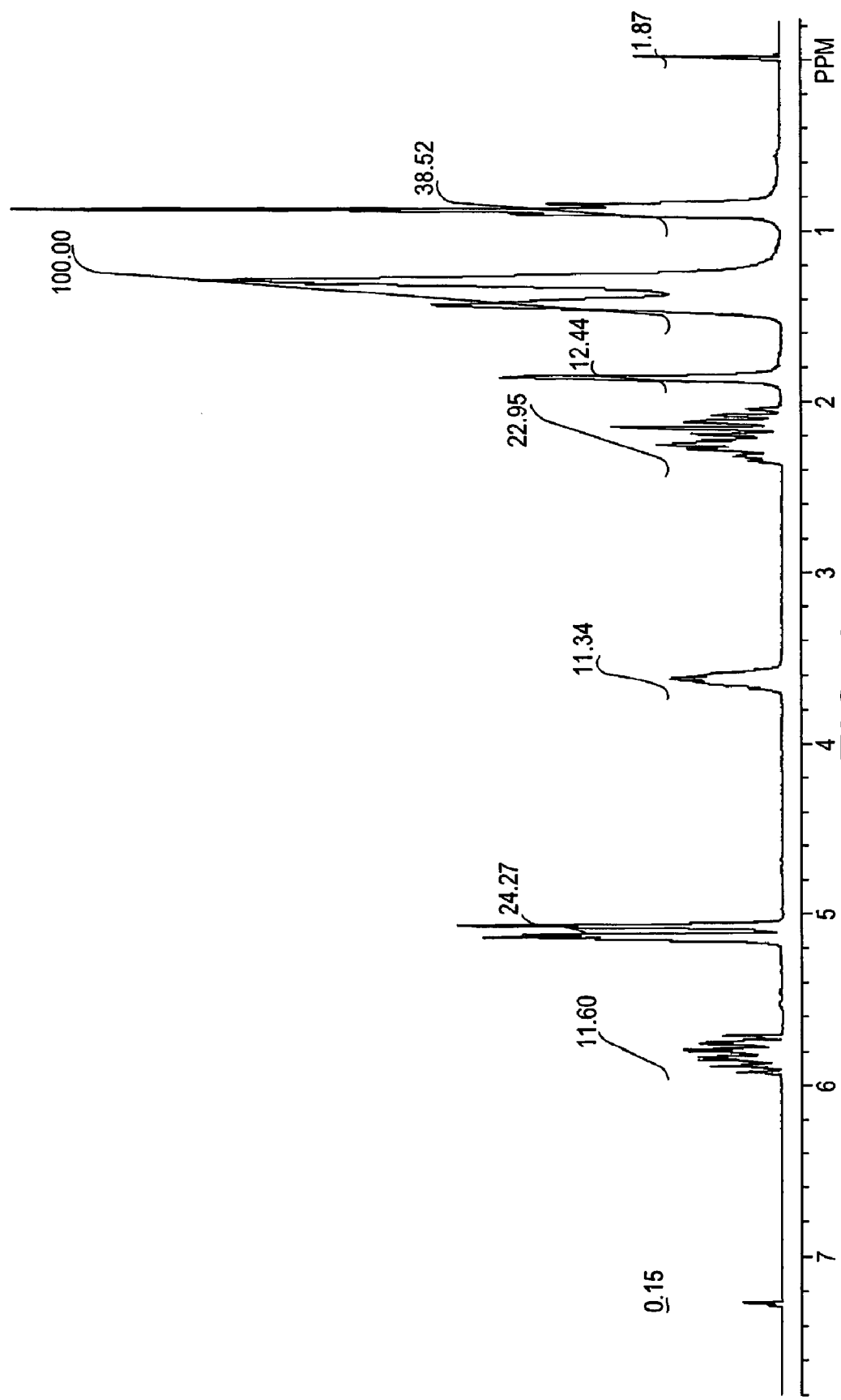
FIG. 3 shows the $^1$H NMR spectra of the product.
Figure 4:
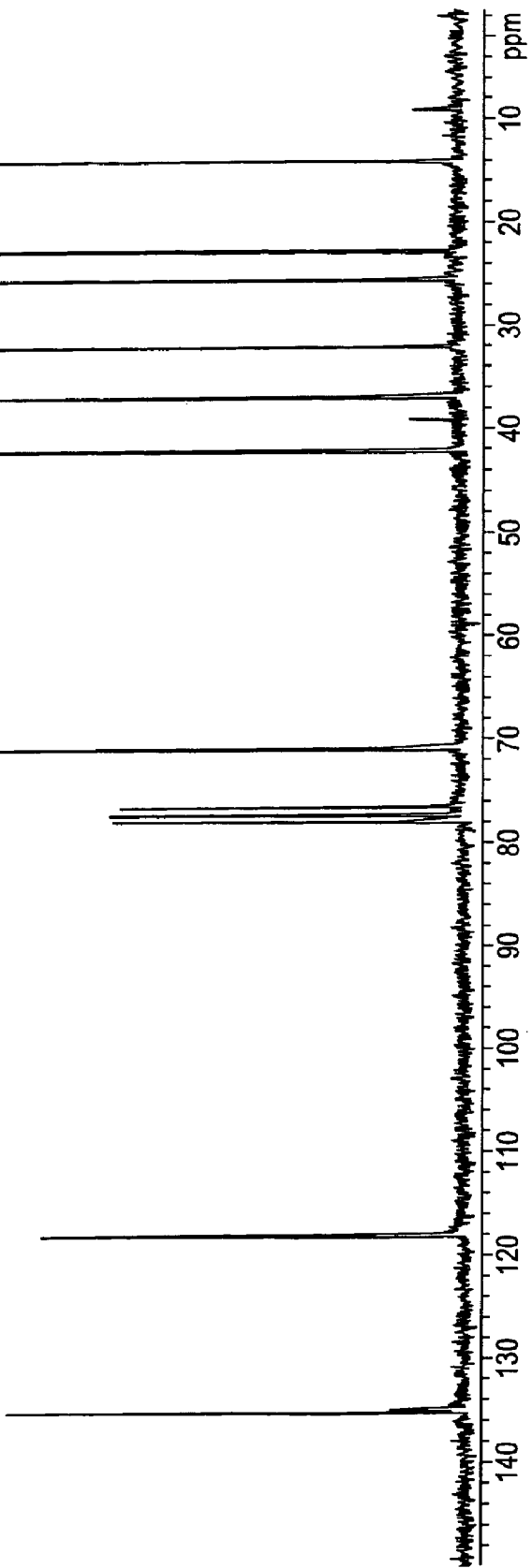
FIG. 4 shows the $^{13}$C NMR spectra of the product.

The reaction was performed in a 2 l autoclave. 500 ml Toluene, 13 g triphenylphosphine (50 mmol) and 0.27 g palladium(II) chloride (1.5 mmol) were added into the autoclave and closed. The autoclave was first flushed two times with N$_2$, then two times with CO and the autoclave was set under 10 bar CO pressure and heated to 80° C. for 2 hours. Then 50 ml degassed water, containing 0.76 g tin(II) chloride dihydrate and 71 g 4-hydroxy-1-nonene (0.5 mol) was added into the reactor. The temperature was increased to 100° C. During the reaction, the CO pressure was maintained at 10 bar. The progress of the reaction was monitored by taking GC samples.

The GC samples indicated that the reaction had proceeded to >99% conversion after 18 hours. At this point the ratio of major product δ-decalactone to biproduct 2-methyl-δ-nonalactone was 4.5:1. The organic layer was separated from the aqueous layer, and the organic layer was then distilled to give the δ-decalactone. The yield of δ-decalactone was 65%.

In an alternative purification procedure, the δ-decalactone product may be distilled directly from the two phase mixture without undergoing a separation step.

Figure 5:
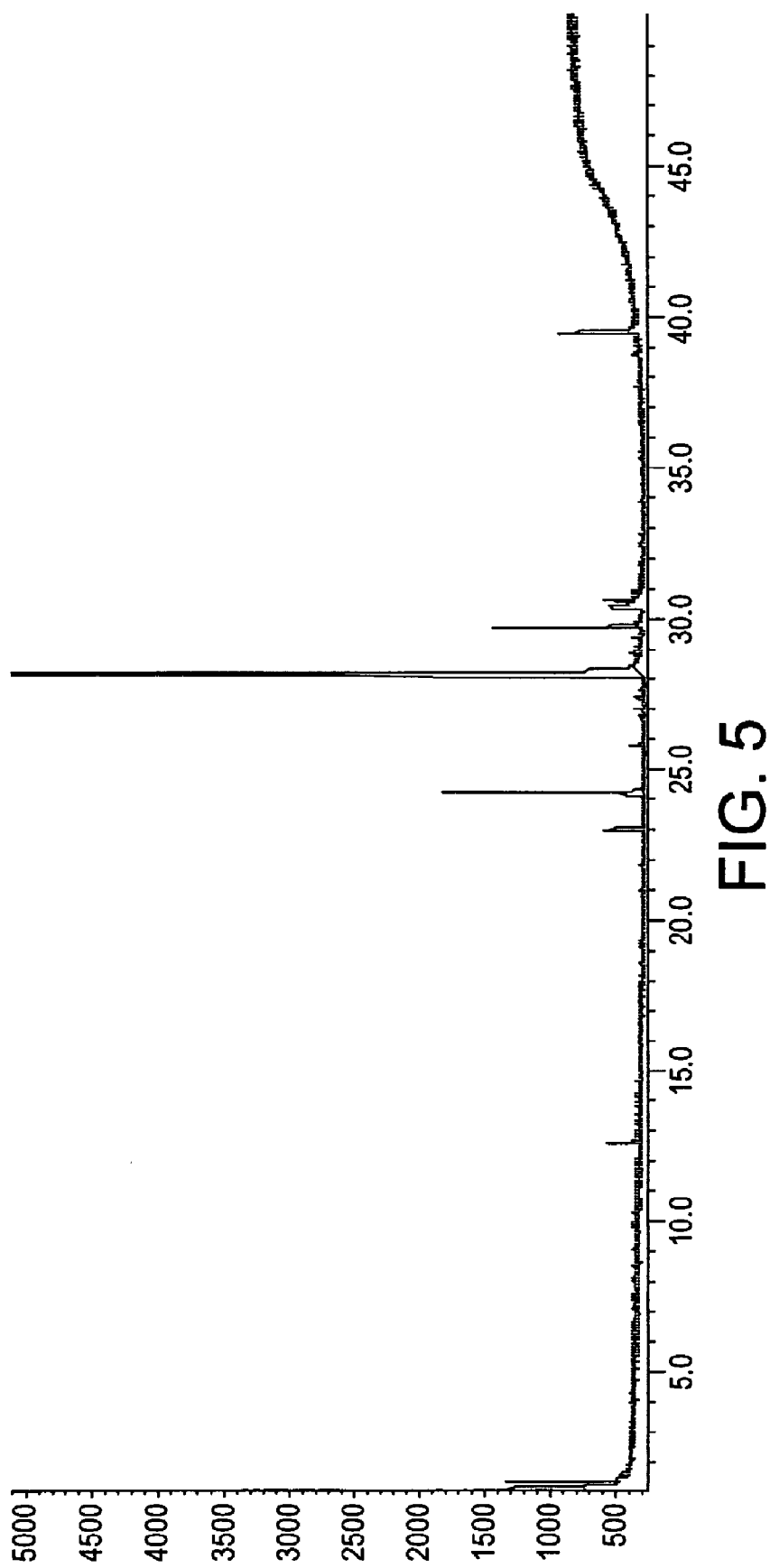

FIG. 5 shows a GC analysis for the distilled product from Example 2. This distilled product contained over 98% δ-decalactone, (peak with a retention time of 28.26) and trace amounts of the biproduct, 2-methyl-γ-nonalactone, (peak with a retention time of 24.21), In addition, trace amounts of a further biproduct (peak with a retention time of 29.71) was shown to be decanoic acid.

Figure 6:
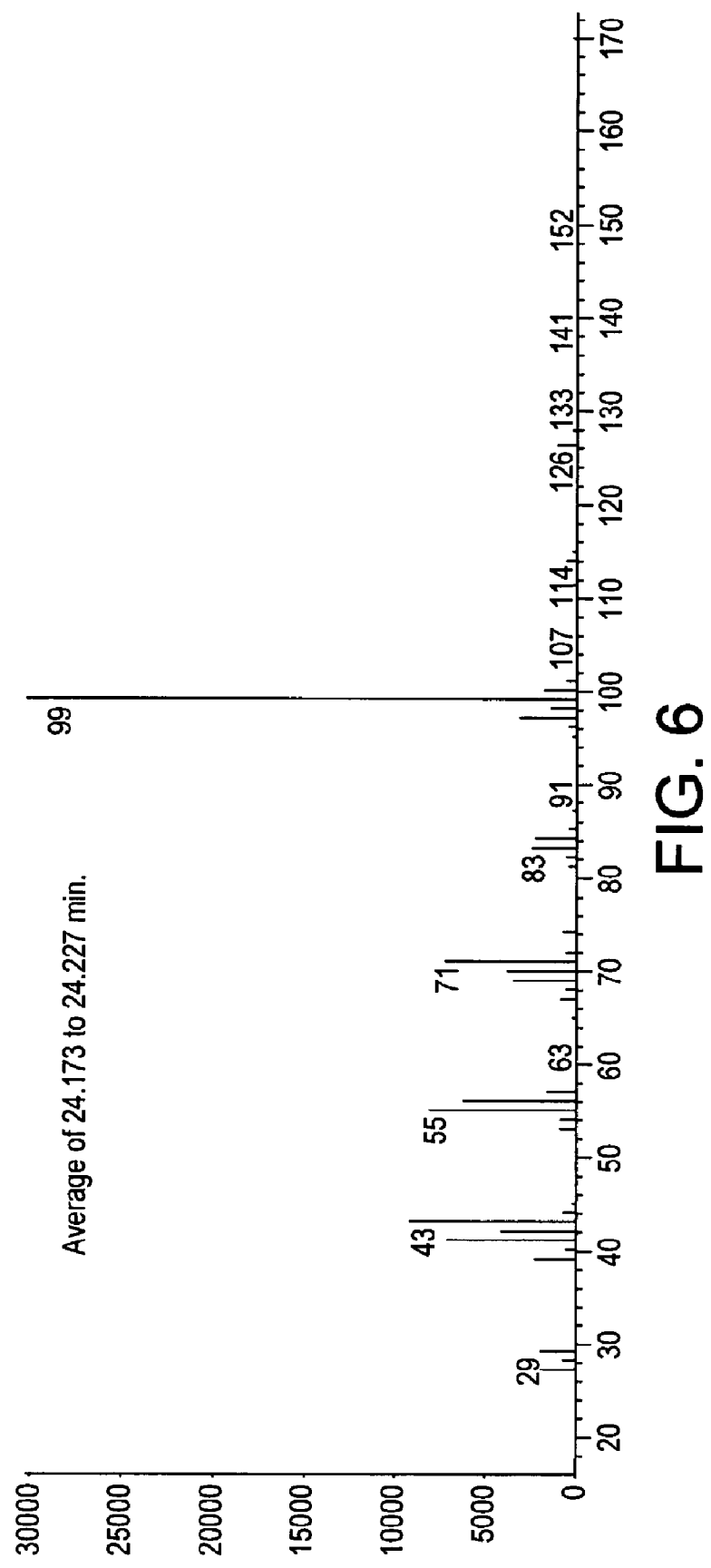

FIG. 6 shows the mass spectra for the biproduct (retention time 24.21).

Figure 7:
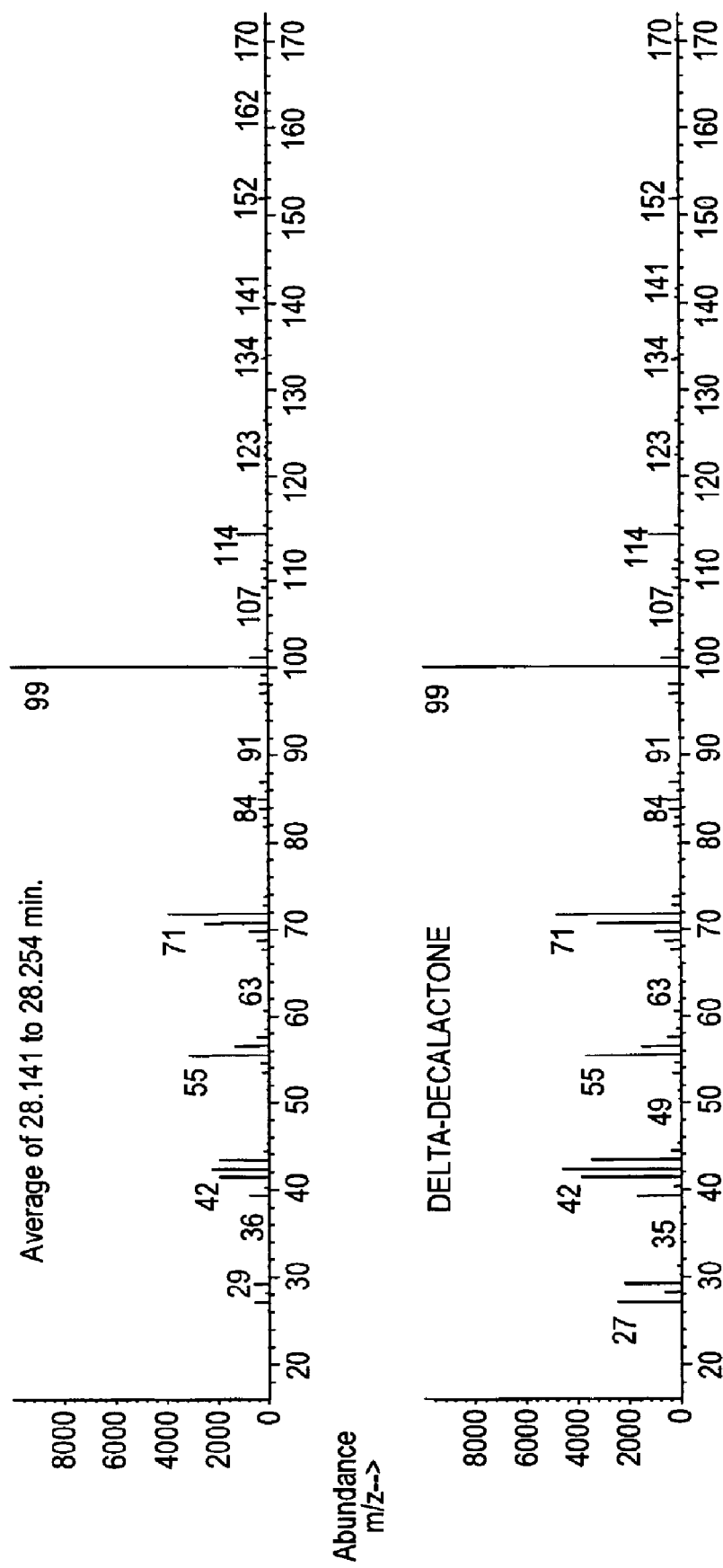

FIG. 7 shows the mass spectra for the major product (retention time 28.26) and as a comparison the mass spectra for a known sample of δ-decalactone.

Figure 8:
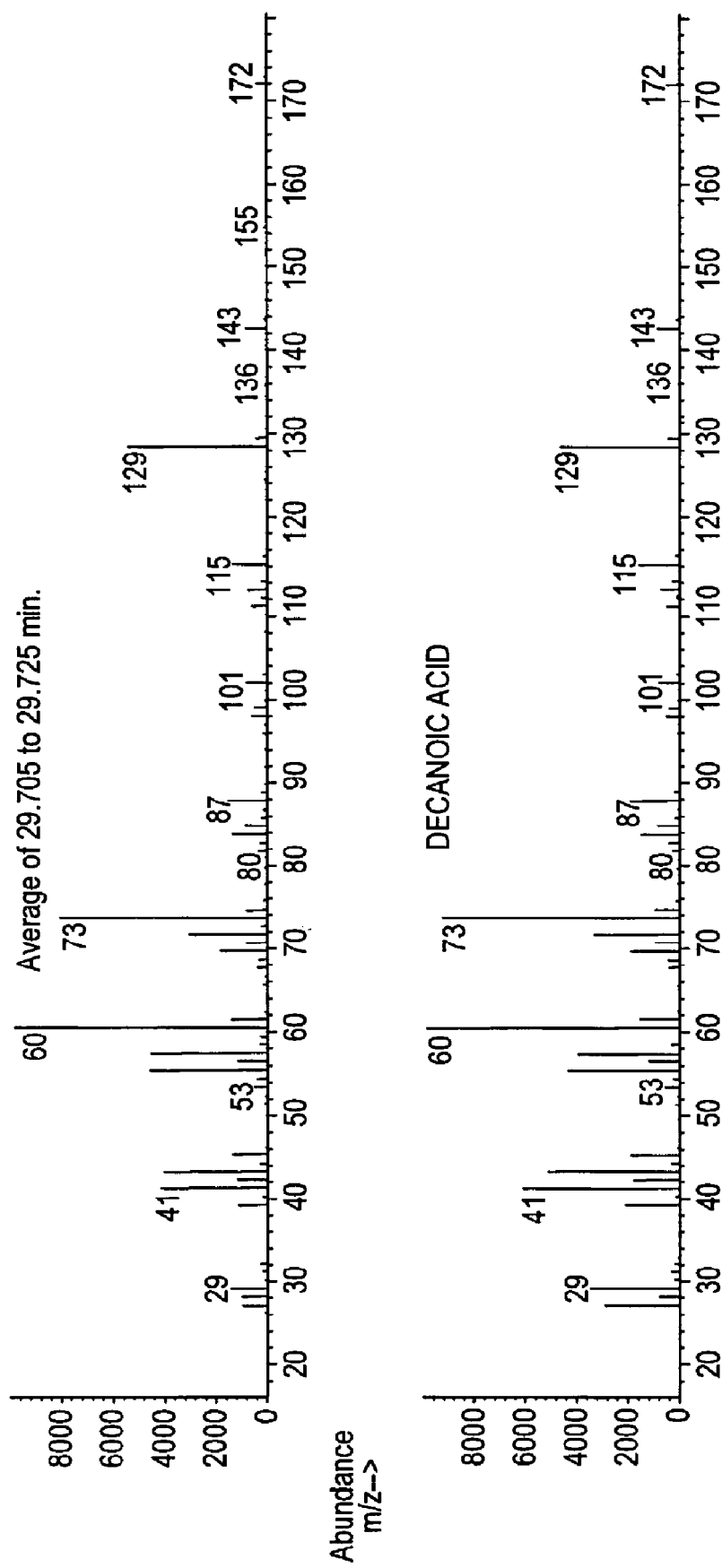

FIG. 8 shows the mass spectra for the further biproduct (retention time 29.71) and as a comparison the mass spectra for a known sample of decanoic acid.

Figure 9:
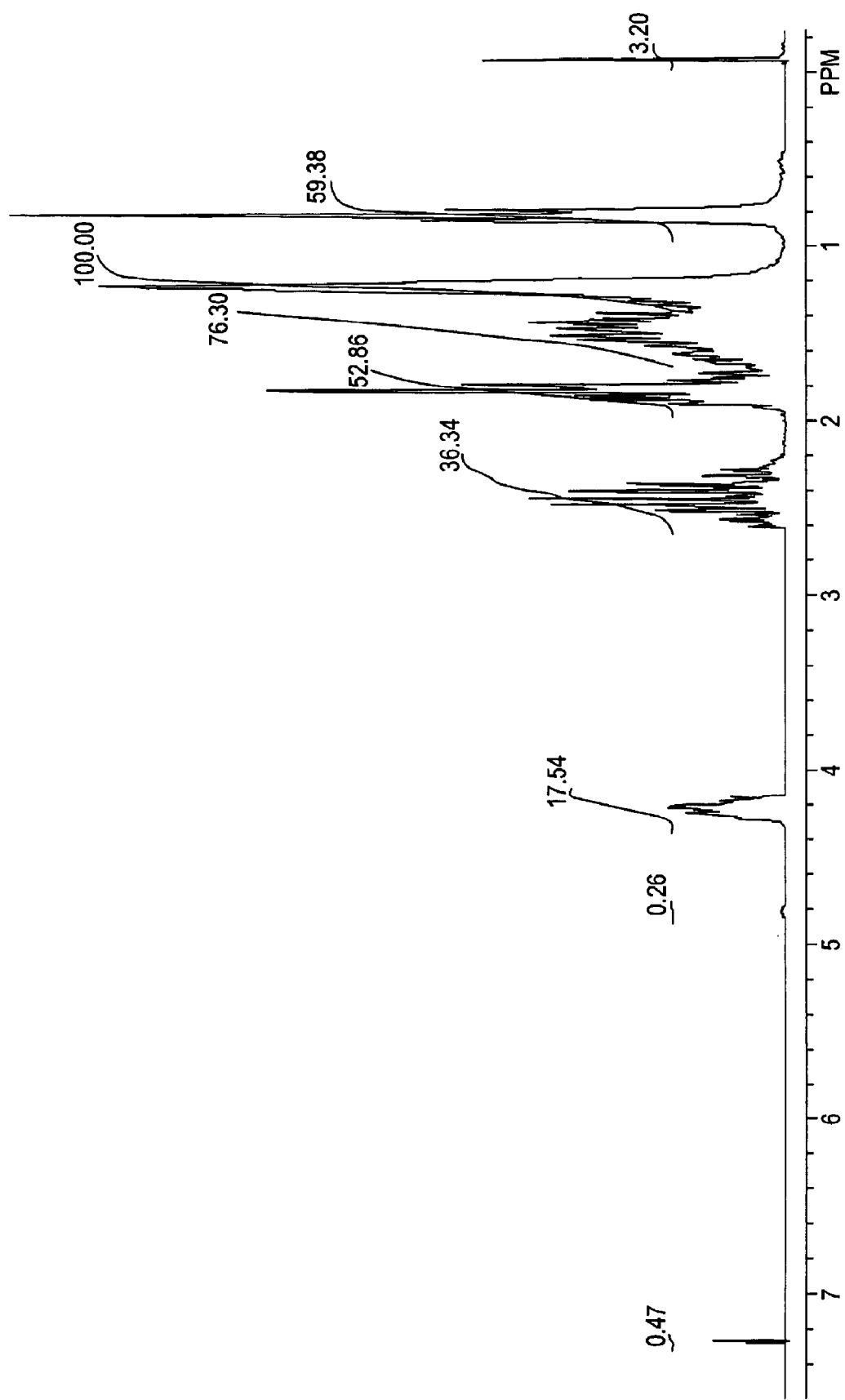

FIG. 9 shows the $^1$H NMR spectra of the major product, δ-decalactone.

Figure 10:
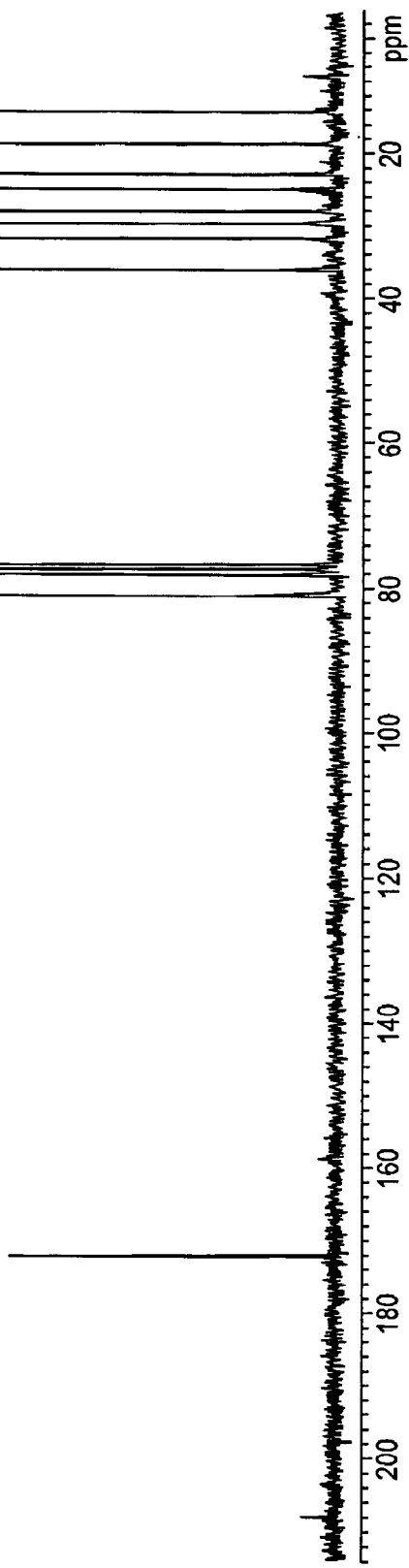

FIG. 10 shows the $^{13}$C NMR spectra of the major product, δ-decalactone.

Example 3

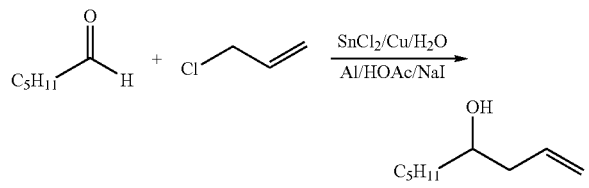

To 500 ml water was added 100 g hexanal (1 mol), 184 g allylchloride (2.4 mol), 19 g tin(II) chloride (0.1 mol), 1.5 g sodium iodide (0.01 mol), 12.5 g copper powder (0.2 mol), 108 g acetic acid (1.8 mol) and 32.4 g aluminium (1.2 mol) (e.g. foil or clips). The reaction mixture was stirred vigorously for ca. 12 h at 35° C. Then the reaction mixture was separated as an aqueous and an organic layer, and the organic layer was distilled in vacuo to give 4-hydroxy-1-nonene (the conversion of starting material (based on hexanal) is typically better than 95%).

Figure 11:
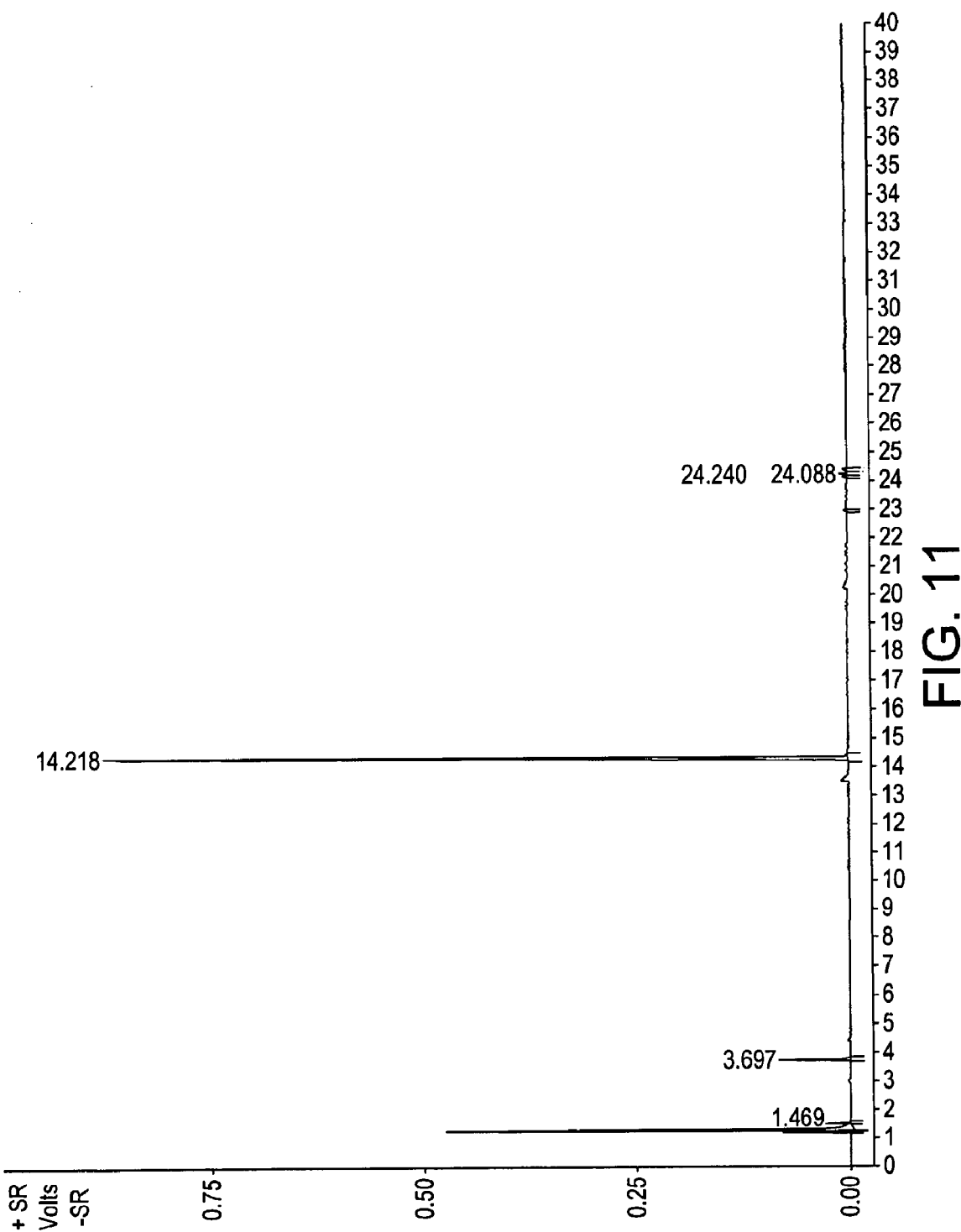

FIG. 11 shows a GC analysis for the crude product (peak with a retention time of 14.29) from Example 3.

Example 4

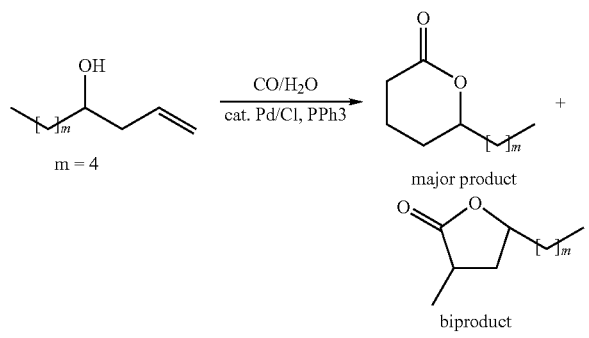

The reaction was performed in a 100 L autoclave. 63 L toluene, 4.5 kg triphenylphosphine (17 mol) and 187.5 g palladium(II)chloride (1.05 mol) was added into the autoclave and closed. The autoclave was first flushed three times with $N_2$, then two times with CO and finally the autoclave was set under 10 bar CO pressure and heated to 80° C. over night. Then 7 L degassed water, containing 477 g tin(II) chloride dihydrate and 10 kg 4-hydroxy-1-nonene (0.5 mol) was pumped into the reactor at a 4 bar CO pressure. The temperature was maintained at 80° C. and the CO pressure was increased to 20 bar. The progress of the reaction was monitored by taking GC samples. After 11.5 h the conversion of 4-hydroxy-1-nonene was 91% and the ratio between delta-lactone to gamma-lactone ca. 6:1. The crude product was distilled in vacuo on a packed column with >40 therorential stages to yield the delta-decalactone (more than 99.3% pure).

Figure 12:
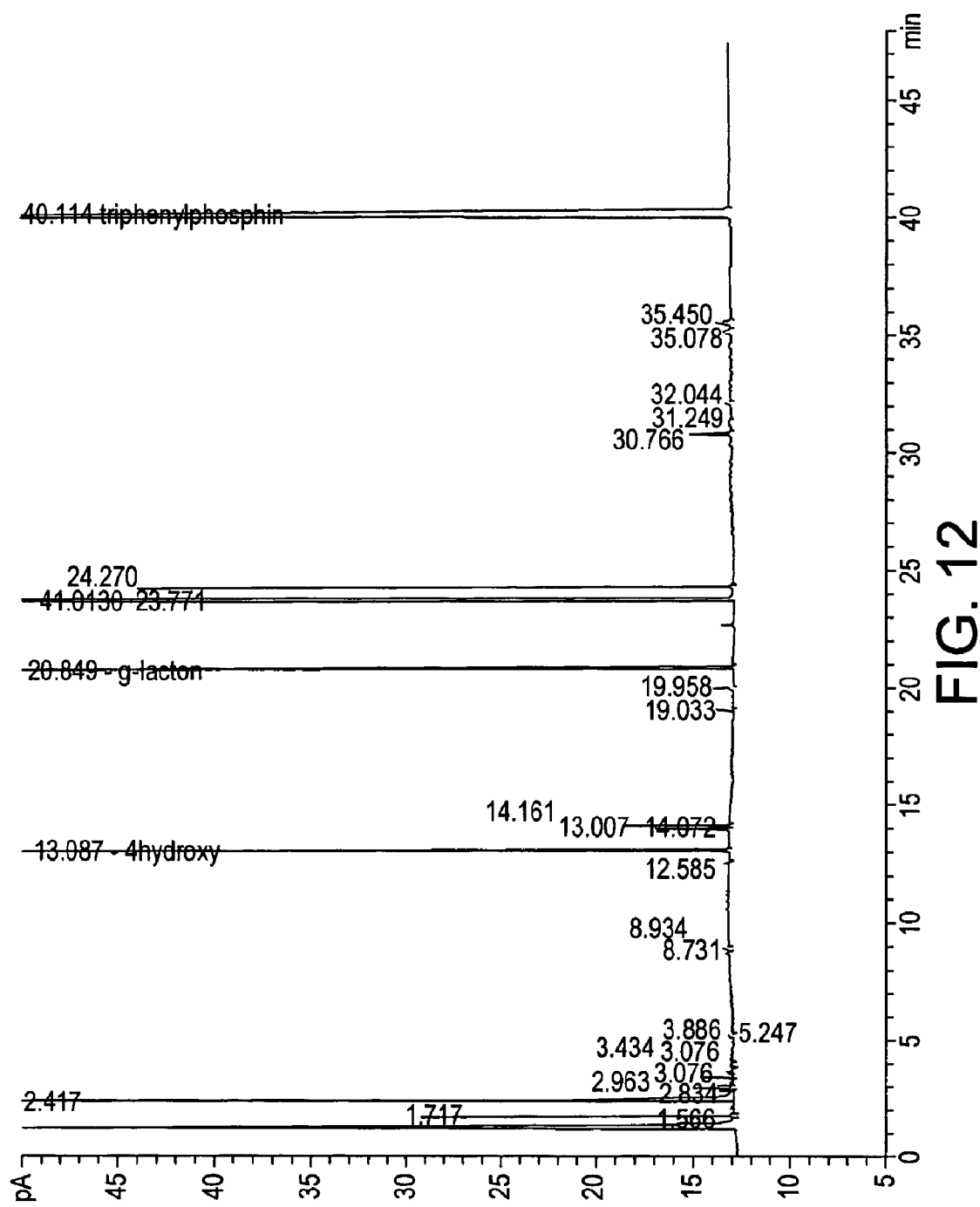

FIG. 12 shows a GC analysis for the crude delta-decalactone product (peak with a retention time of 23.77) from Example 4.

FIG. 13 shows a GC analysis for the distilled delta-decalactone product (peak with a retention time of 23.87) from Example 4.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention will now be further described by the following numbered paragraphs:

1. A process for preparing a lactone comprising the steps of:

reacting a carbonyl compound selected from a group consisting of an aldehyde and a ketone with an organic halide in a carbon chain extension reaction to form an alcohol compound comprising a functional group capable of allowing for carbonylation of said alcohol compound;

reacting said alcohol compound in a carbonylation reaction to form an hydroxycarboxylic acid; and cyclising the hydroxycarboxylic acid to produce the lactone.

2. A process according to paragraph 1 wherein the carbonyl compound is of Formula IVa

wherein $R_{1A}$ is a hydrocarbyl group, and $R_{1B}$ is selected from hydrogen and a hydrocarbyl group.

3. A process according to paragraph 2, wherein $R_{1A}$ is a $C_1$-$C_8$ alkyl group optionally substituted with one or more hydrocarbyl or oxyhydrocarbyl groups.

4. A process according to paragraph 2 or 3, wherein $R_{1A}$ is a $C_5$-$C_7$ alkyl group.

5. A process according to any one of paragraphs 2 to 4, wherein $R_{1B}$ is a $C_1$-$C_8$ alkyl group optionally substituted with one or more hydrocarbyl or oxyhydrocarbyl groups.

6. A process according to paragraph 2, wherein $R_{1B}$ is hydrogen.

7. A process according to any of the preceding paragraphs, wherein the organic halide is an unsaturated organic halide.

8. A process according to any one of the preceding paragraphs wherein the organic halide is an unsaturated halide of the Formula IIIb:

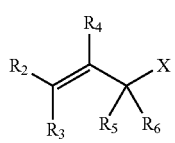

wherein $R_2$, $R_3$, $R_4$, $R_5$ and $R_6$ are independently selected from a group comprising a hydrogen and a hydrocarbyl group; and X is a halide.

9. A process according to paragraph 8, wherein $R_2$, $R_3$, $R_4$, $R_5$ and $R_6$ are independently selected from a group comprising hydrogen and a $C_1$-$C_4$ alkyl group.

10. A process according to any of the preceding paragraphs, wherein the organic halide is allyl chloride.

11. A process according to any of the preceding paragraphs, wherein the carbon chain extension reaction uses a catalyst comprising a metal and/or a salt of a metal wherein the metal is selected from aluminium, antimony, bismuth, cadmium, copper, indium, lead, tin, magnesium, manganese, zinc and mixtures thereof.

12. A process according to paragraph 11, wherein the catalyst in the carbon chain extension reaction comprises a mixture of aluminium, copper, tin(II) chloride and sodium iodide.

13. A process according to any of the preceding paragraphs, wherein the carbon chain extension reaction is carried out in water.

14. A process according to any of the preceding paragraphs, wherein the carbonylation reaction comprises reacting the alcohol compound with a source of carbon monoxide.

15. A process according to paragraph 14, wherein the source of carbon monoxide is carbon monoxide.

16. A process according to paragraph 14, wherein the source of carbon monoxide is formic acid.

17. A process according to paragraph 14, wherein the source of carbon monoxide is oxalic acid.

18. A process according to any of the preceding paragraphs, wherein carbonylation reaction uses a catalytic system comprising a transition metal and/or a salt of a transition metal wherein the transition metal is selected from cobalt, iridium, palladium, platinum, rhodium, and mixtures thereof.

19. A process according to paragraph 18, wherein the carbonylation reaction catalytic system comprises palladium chloride.

20. A process according to paragraph 18 or 19, wherein the carbonylation reaction catalytic system further comprises a ligand comprising at least one donor atom selected from nitrogen, phosphorous, arsenic, antimony and bismuth.

21. A process according to paragraph 20, wherein the ligand is triphenylphosphine.

22. A process according to any one of paragraphs 18 to 21, wherein the catalytic system further comprises a tin(II) chloride co-catalyst.

23. A process according to any of the preceding paragraphs, wherein carbonylation reaction is carried out at a temperature of from 80 to 140° C.

24. A process according to any of the preceding paragraphs, wherein carbonylation reaction is carried out at a pressure of from 1 to 150 bara.

25. A process according to any of the preceding paragraphs, wherein carbonylation reaction is carried out in the presence of water.

26. A process according to any of the preceding paragraphs, wherein the lactone produced is a delta-lactone.

27. A process according to any of the preceding paragraphs, which further comprises the step of purifying the lactone.

28. A process according to paragraph 27, wherein the step of purifying the lactone comprises distillation of the lactone.

29. A process for preparing a delta-lactone comprising the steps of a) reacting an aldehyde with an unsaturated organic halide in a carbon chain extension reaction, using a catalyst comprising a metal and/or a salt of a metal wherein the metal is selected from aluminium, antimony, bismuth, cadmium, copper, indium, lead, tin, magnesium, manganese, sodium, zinc and mixtures thereof, to form an alcohol compound comprising a functional group capable of allowing for carbonylation of said alcohol compound;

b) reacting said alcohol compound with a source of carbon monoxide in a carbonylation reaction in the presence of water, using a catalytic system comprising a transition metal and/or a salt of a transition metal wherein the transition metal is selected from cobalt, iridium, palladium, platinum, rhodium, and mixtures thereof, and a ligand comprising at least one donor atom selected from nitrogen, phosphorous, arsenic, antimony and bismuth to form an hydroxycarboxylic acid; and c) cyclising the hydroxycarboxylic acid to produce the delta-lactone.

30. A process for preparing a delta-lactone according to paragraph 29, wherein the process further comprises a step:

d) purifying the delta-lactone.

31. A process for preparing a delta-lactone according to paragraph 30, wherein step d) comprises distillation of the lactone.

32. Use of a lactone obtained according to any one of the process paragraph 1 to 31, as a food flavouring.

33. A method of flavouring a food material comprising contacting a lactone obtained according to any one of the process paragraph 1 to 31 with at least one other food ingredient.

34. A method of preparing a food or a food ingredient, comprising admixing a lactone obtained according to any one of the process paragraph 1 to 31 with at least one other food ingredient.

35. A food or a food ingredient comprising a lactone obtained according to any one of the process paragraph 1 to 31 and with at least one other food ingredient.

36. A process for preparing a lactone substantially as hereinbefore described with reference to the examples.

The invention claimed is:

1. A process for preparing a delta-lactone comprising the steps of
   a) reacting an aldehyde with an unsaturated organic halide in a carbon chain extension reaction, wherein the carbon chain extension reaction is carried out in the presence of water, using a catalyst comprising a mixture of aluminum, copper, tin(II) chloride and sodium iodide or a catalyst comprising a mixture of copper and tin(II) chloride, to form an alcohol compound comprising a functional group capable of allowing for carbonylation of said alcohol compound;
   b) reacting said alcohol compound with a source of carbon monoxide in a carbonylation reaction in the presence of water, using a catalytic system comprising a transition metal and/or a salt of a transition metal wherein the transition metal is selected from cobalt, iridium, palladium, platinum, rhodium, and mixtures thereof, wherein the catalytic system further comprises a tin(II) chloride co-catalyst and a ligand comprising at least one donor atom selected from nitrogen, phosphorous, arsenic, antimony and bismuth to form an hydroxycarboxylic acid; and
   c) cyclising the hydroxycarboxylic acid to produce the delta-lactone.

2. A process for preparing a delta-lactone according to claim 1, wherein the process further comprises a step:
   d) purifying the delta-lactone.

3. A process for preparing a delta-lactone according to claim 2, wherein step d) comprises distillation of the lactone.

4. A process according to claim 1 wherein the aldehyde compound is of Formula IVa,

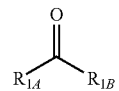

wherein $R_{1A}$ is a hydrocarbyl group, and $R_{1B}$ is hydrogen.

5. A process according to claim 4, wherein $R_{1A}$ is a $C_1$-$C_8$ alkyl group optionally substituted with one or more hydrocarbyl or oxyhydrocarbyl groups.

6. A process according to claim 4, wherein $R_{1A}$ is a $C_5$-$C_7$ alkyl group.

7. A process according to claim 1 wherein the organic halide is an unsaturated halide of the Formula IIIb:

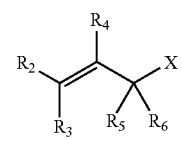

wherein $R_2$, $R_3$, $R_4$, $R_5$ and $R_6$ are independently selected from a group comprising a hydrogen and a hydrocarbyl group; and X is a halide.

8. A process according to claim 7, wherein $R_2$, $R_3$, $R_4$, $R_5$ and $R_6$ are independently selected from a group comprising hydrogen and a $C_1$-$C_4$ alkyl group.

9. A process according to claim 1, wherein the organic halide is allyl chloride.

10. A process according to claim 1, wherein the source of carbon monoxide is carbon monoxide.

11. A process according to claim 1, wherein the source of carbon monoxide is formic acid.

12. A process according to claim 1, wherein the source of carbon monoxide is oxalic acid.

13. A process according to claim 1, wherein the carbonylation reaction catalytic system comprises palladium chloride.

14. A process according to claim 1, wherein the carbonylation reaction catalytic system further comprises a ligand comprising at least one donor atom selected from nitrogen, phosphorous, arsenic, antimony and bismuth.

15. A process according to claim 13, wherein the ligand is triphenylphosphine.

16. A process according to claim 1, wherein carbonylation reaction is carried out at a temperature of from 80 to 140° C.

17. A process according to claim 1, wherein carbonylation reaction is carried out at a pressure of from 1 to 150 bara.

* * * * *